United States Patent [19]

Boebel

[11] Patent Number: 4,620,547

[45] Date of Patent: Nov. 4, 1986

[54] INSTRUMENT FOR SAMPLING TISSUE SPECIMENS

[75] Inventor: Manfred Boebel, Oetischeim, Fed. Rep. of Germany

[73] Assignee: Richard Wolf GmbH, Knittlingen, Fed. Rep. of Germany

[21] Appl. No.: 687,195

[22] Filed: Dec. 28, 1984

[30] Foreign Application Priority Data

Dec. 31, 1983 [DE] Fed. Rep. of Germany ....... 3347671

[51] Int. Cl.$^4$ ................................................ A61B 6/00
[52] U.S. Cl. .......................................... 128/754; 128/4
[58] Field of Search ............... 128/634, 751, 752, 753, 128/754, 757, 758, 4, 6

[56] References Cited

U.S. PATENT DOCUMENTS

| | | | |
|---|---|---|---|
| 2,708,437 | 5/1955 | Hutchins | 128/751 |
| 3,590,808 | 7/1971 | Muller | 128/752 |
| 3,606,878 | 9/1971 | Kellogg, Jr. | 128/753 |
| 4,254,762 | 3/1981 | Yoon | 128/4 |
| 4,340,066 | 7/1982 | Shah | 128/751 |
| 4,396,021 | 8/1983 | Baumgartner | 128/751 |
| 4,503,843 | 3/1985 | Boebel | 128/4 |

Primary Examiner—William E. Kamm
Attorney, Agent, or Firm—Hill, Van Santen, Steadman & Simpson

[57] ABSTRACT

The instrument for sample tissue specimens comprises an inner shaft extending eccentrically through a distally closed outer shaft and intended for reception of an optical system comprising a lateral objective, which inner shaft is distally connected or connectible to a cutting edge which cooperates with an edge of a distal lateral viewing and cutting aperture in the outer shaft acting as a mating cutting edge over the area of this distal lateral aperture by axial displacement of the inner shaft within the outer shaft.

4 Claims, 3 Drawing Figures

INSTRUMENT FOR SAMPLING TISSUE SPECIMENS

BACKGROUND OF THE INVENTION

1. Field of the Invention

The invention relates to an endoscopic instrument for internally sampling tissue specimens under constant visual inspection, comprising a shaft having a closed distal (i.e. leading) end and having a lateral viewing and cutting aperture near said closed end, which may be coupled to a negative pressure for example via a suction passage and whereof the rim forms a mating cutting edge which cooperates with a cutting edge displaceable within the shaft.

2. Description of the Prior Art

To obtain tissue samples from bodily cavities, which are to be examined, in particular of trophoblast tissue which encloses the "growth" bag of an embryo, it is known to lead a cannula or a biopsy forceps to the tissue which is to be examined to sample a tissue specimen under ultrasonic monitoring or visual observation by means of an optical system. If use is made of ultrasonic monitoring, the disadvantage exists that no direct observation is possible, and if use is made of biopsy forceps under endoscopic observation, the tissue specimens are commonly quantitatively inadequate for examination.

Shafts connectible to a negative pressure and comprising a distal head which is equipped with a lateral aperture the rim of which forms a mating cutting edge for a cutting blade movable within the head, are also known for sampling tissue specimens. These instruments may be led up to the point in question of the tissues but without visual observation, or else under complex X-ray monitoring.

SUMMARY OF THE INVENTION

One object of the invention consists in devising a single instrument comprising a shaft of as small a diameter as possible, which by virtue of unobstructed observation renders it possible to make a visual selection or approach to the locus of the tissue specimen which is to be sampled, and then to remove the required quantity of the tissue which is to be examined, under constant observation.

In the case of the initially defined instrument according to the invention, this problem is resolved in that an inner shaft intended to receive an optical system comprising a lateral objective and extending eccentrically through a distally closed outer shaft is distally connected or connectible to the cutting edge which cooperates with the inner rim of the aperture acting as a mating cutting edge over the area of this lateral aperture of the outer shaft by axial displacement of the inner shaft within the outer shaft.

An uncomplicated solution for sampling tissue specimens under direct and constant observation is possible thereby. Thanks to the eccentric position of the inner shaft within the outer shaft, a passage is formed in the outer shaft which may be connected to a negative pressure and through which tissue sections may be drawn by suction into the lateral aperture of the outer shaft and then separated by axial displacement of the inner shaft by means of its distal blade and drawn off by suction through the passage. Whilst doing so, the tissue area in question may be identified rapidly and simply through the lateral viewing and cutter aperture at the distal side, as remains to be described in particular, adequate tissue quantities being obtained for examination in any case.

The invention is described in the following with reference to the drawings which an example of embodiment is illustrated.

DETAILED DESCRIPTION OF THE PREFERRED EMBODIMENT

Figure 1:
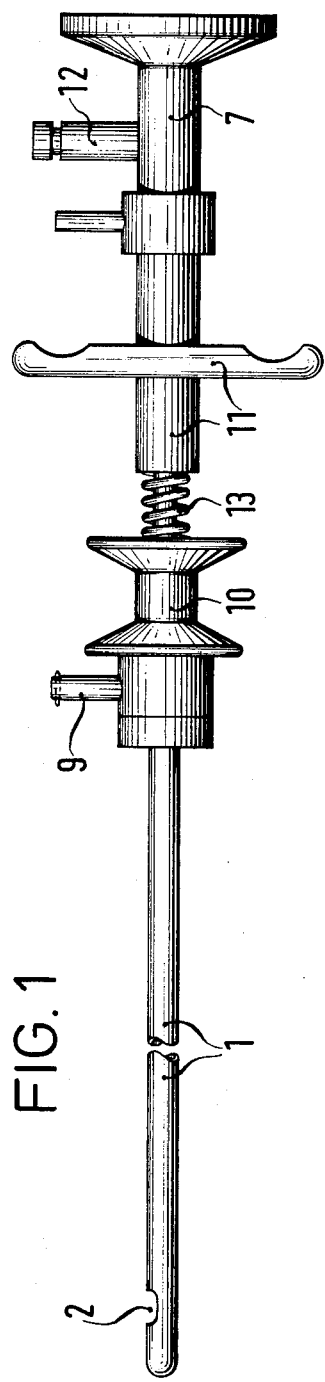
FIG. 1 shows a sideview of the instrument in accordance with the invention.
Figure 3:
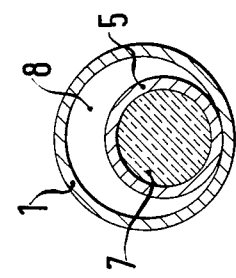
FIG. 3 shows a cross-section along the line III to III of FIG. 2.
Figure 2:
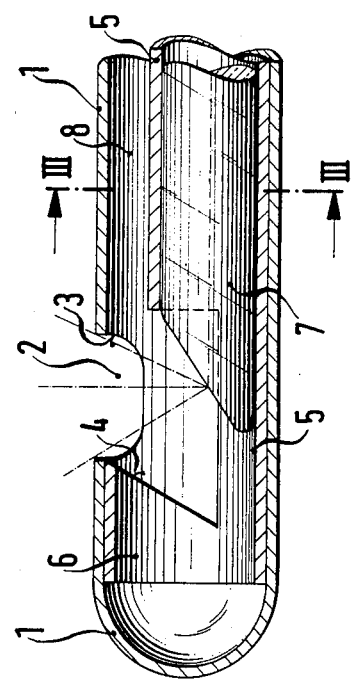
FIG. 2 shows an axial cross-section through the distal extremity of the instrument according to FIG. 1 to enlarged scale.

The instrument comprises an outer shaft 1 which is closed at its distal end and has near said closed end a lateral aperture or opening 2 a rim portion of which forms a mating cutting edge 3 cooperating with a cutting edge 4 of a cutter 6 which is connected or is connectible to the distal extremity of an inner shaft 5. The inner shaft 5 which comprises an optical system 7, which has a lateral objective, extends eccentrically through the outer shaft 1 and thereby forms a sickle-shaped suction passage 8 with the outer shaft, which passage may be connected to a source of negative pressure via a pipe stub 9. The cutter 6 is joined fixedly or releasably to the untwistable and axially displaceable inner shaft 5 by means known per se such as screw-threads or the like and in the case of the illustrated example is formed by an integral annular extension of the inner shaft 5. The extension or ring which is at the distal end of the shaft 5 is enlarged to the internal diameter of the outer shaft at the distal side of the objective of the optical system.

The outer shaft 1 is proximally connected to a first handle 10 in a fixed and untwistable manner, and the inner shaft 5 terminates proximally in a second handle member 11 to which may be coupled the optical system 7 which is connectible to a light source via a light ductor cable by means of the lateral connector stub 12.

A compression spring 13, by virtue of whose spring action the inner shaft 5 may be displaced in a proximal direction so far that the cutter 6 closes off the aperture 2 of the outer shaft 1, is situated under cover within the handle member 11 between the two handle members 10 and 11.

For sampling a tissue specimen, the outer shaft is inserted into the bodily cavity, for example into the uterus via the cervical passage. The two handle members 10 and 11 are then pressed together, thereby displacing the inner shaft 5 so far within the outer shaft 1 in the distal direction that the aperture 2 is open for viewing by means of the optical system 7. The area of tissue in question may thereby be identified by observation. Under this direct and constant observation, the instrument may now have the aperture 2 led to the locus of the tissue which is to be examined, and the passage 8 may be connected to the negative pressure, whereby tissue is drawn by suction into the aperture 2 and cut off by means of the cutting edge 4 of the cutter 6 by releasing the handle 10,11 and displacing the inner shaft 5 by means of the spring loading 13, and drawn off by suction via the passage 8.

Since the optical system allows of directional setting within the uterus or in the bodily cavity, as well as of inspection of the tissue specimen drawn by suction into the cutter aperture, it is simple to select, inspect and extract the specimen quantity required without the instrument or parts thereof having to be removed from the uterus and possibly reinserted into the uterus again repeatedly.

So that the fibrous tissue which is to be severed and extracted may be inserted more satisfactorily into the cutter aperture 2, it is possible to lead a small quantity of fluid to the tissue to raise the fibres, before applying a negative pressure via the suction passage 8.

In a further embodiment of the invention, it is possible to secure the outer shaft releasably on the handle member 10 by means of a screw-threaded ring or the like, for easy replacement as well as cleaning of the outer and inner shafts. So that the sickle-shaped passage formed between the inner and outer shafts may be enlarged complementarily, it is also possible furthermore to construct the inner shaft in a manner such that the same enflanks the optical system in a partial manner only.

What is claimed is:

1. An instrument for sampling tissue specimens under constant visual inspection comprising a hollow outer shaft enclosing an axial passage and having a closed distal end, said shaft having a lateral aperture adjacent said closed distal end with a proximal edge of said aperture forming a first cutting edge, an inside shaft having a first portion of a smaller diameter than the inner diameter of the outer shaft, means for mounting the inside shaft within the outer shaft with the first portion being eccentrically positioned in the outer shaft, said means enabling axial reciprocal movement between the inside and outer shafts, said inside shaft having an optical system having a portion terminating adjacent a distal end of the first portion of the inside shaft to enable viewing through said aperture, an outer surface of the first portion of the inside shaft and the inner surface of the outer shaft form a space therebetween, said space having means for connecting to a source of suction to form an extraction channel, an enlarged annular ring-shaped portion forming an annular cutter having a diameter corresponding to the inner diameter of the outer shaft with one edge of the cutter forming a second cutting edge cooperating with the first cutting edge, said annular cutter being connected to a distal end of the first portion of the inside shaft and means for shifting the inside shaft relative to the outer shaft so that axial movement of the inside shaft to shift the first and second cutting edges together will cut a specimen extending through said aperture.

2. An instrument according to claim 1, wherein the means for shifting the inside shaft and the outer shaft includes a handle connected to the outer shaft and a handle connected to the inside shaft.

3. An instrument according to claim 2, wherein said means for shifting includes a spring disposed between said handles to axially shift the handles to a position to cause the second cutting edge to move into cutting engagement with the first cutting edge.

4. An instrument according to claim 1, wherein said annular ring-shaped portion is an integral part of the inside shaft.

* * * * *